(12) United States Patent
Hirano et al.

(10) Patent No.: US 11,571,381 B2
(45) Date of Patent: Feb. 7, 2023

(54) COMPOSITION FOR FORMING COATING (71) Applicant: KAO CORPORATION, Tokyo (JP)

(72) Inventors: Takahiro Hirano, Utsunomiya (JP); Takehiko Tohjo, Utsunomiya (JP); Tatsuya Yoshino, Funabashi (JP)

(73) Assignee: KAO CORPORATION, Tokyo (JP)

( * ) Notice: Subject to any disclaimer, the term of this patent is extended or adjusted under 35 U.S.C. 154(b) by 87 days.

(21) Appl. No.: 16/603,399

(22) PCT Filed: Apr. 19, 2018

(86) PCT No.: PCT/JP2018/016184
§ 371 (c)(1),
(2) Date: Oct. 7, 2019

(87) PCT Pub. No.: WO2018/194130
PCT Pub. Date: Oct. 25, 2018

(65) Prior Publication Data
US 2020/0030222 A1 Jan. 30, 2020

(30) Foreign Application Priority Data
Apr. 19, 2017 (JP) .............................. JP2017-082840

(51) Int. Cl.
| | | |
|---|---|---|
| A61K 8/87 | (2006.01) | |
| A45D 34/04 | (2006.01) | |
| A61K 8/41 | (2006.01) | |
| A61K 8/44 | (2006.01) | |
| A61K 8/81 | (2006.01) | |
| A61Q 1/00 | (2006.01) | |
| D06M 13/12 | (2006.01) | |
| D06M 13/144 | (2006.01) | |
| D06M 15/39 | (2006.01) | |
| D06M 15/564 | (2006.01) | |

(52) U.S. Cl.
CPC .............. *A61K 8/87* (2013.01); *A45D 34/04* (2013.01); *A61K 8/416* (2013.01); *A61K 8/442* (2013.01); *A61K 8/8129* (2013.01); *A61Q 1/00* (2013.01); *D06M 13/12* (2013.01); *D06M 13/144* (2013.01); *D06M 15/39* (2013.01); *D06M 15/564* (2013.01); *A45D 2200/057* (2013.01); *A61K 2800/596* (2013.01); *A61K 2800/83* (2013.01); *A61K 2800/87* (2013.01)

(58) Field of Classification Search
CPC ...... A61K 8/416; A61K 8/442; A61K 8/8129; A61K 2800/596; A61K 2800/83; A61K 2800/87; A61K 2800/805; A61K 8/046; A61K 8/34; A61K 8/35; A61K 8/44; A61K 8/87; A61Q 1/00; D06M 13/12; D06M 13/144; D06M 15/39; D06M 15/564; A45D 2200/057; D01D 5/0084; B05B 5/0538; B05B 5/035
See application file for complete search history.

(56) References Cited

U.S. PATENT DOCUMENTS

| | | | |
|---|---|---|---|
| 6,311,903 B1 | 11/2001 | Gaw et al. | |
| 6,514,504 B1 | 2/2003 | Yen et al. | |
| 6,531,142 B1 | 3/2003 | Rabe et al. | |
| 7,078,046 B1 | 7/2006 | Rabe et al. | |
| 7,823,809 B2 * | 11/2010 | Yamaguchi | B05B 5/0533 239/690.1 |
| 2003/0012753 A1 | 1/2003 | Simon | |
| 2009/0035381 A1 * | 2/2009 | Stankus | A61K 9/5073 514/1.1 |
| 2010/0015460 A1 * | 1/2010 | Heiskanen | D21H 23/50 428/537.5 |
| 2013/0058880 A1 * | 3/2013 | Dong | A61K 8/28 424/63 |
| 2018/0317627 A1 * | 11/2018 | Fukuda | A61K 8/046 |

FOREIGN PATENT DOCUMENTS

| | | |
|---|---|---|
| CN | 102534835 A | 7/2012 |
| EP | 3 366 270 A1 | 8/2018 |
| EP | 3 366 271 A1 | 8/2018 |
| EP | 375022 A1 | 12/2020 |
| JP | 62-501003 A | 4/1987 |
| JP | 2003-507165 A | 2/2003 |
| JP | 2003-160438 A | 6/2003 |
| JP | 2006-77031 A | 3/2006 |
| MA | 2006-104211 A | 4/2006 |
| WO | WO 86/02546 A1 | 5/1986 |
| WO | WO 94/11119 A1 | 5/1994 |
| WO | WO 98/03267 A1 | 1/1998 |

(Continued)

OTHER PUBLICATIONS

Yener Electrospinning of PVB, e-Polymers, p. 1, May 2013.*

(Continued)

*Primary Examiner* — Matthew P Coughlin
*Assistant Examiner* — Thurman Wheeler
(74) *Attorney, Agent, or Firm* — Oblon, McClelland, Maier & Neustadt, L.L.P.

(57) ABSTRACT

Provided is a method for forming a good fibrous coating on a target surface even in a high-humidity environment when electrostatically spraying is performed directly on the target surface such as skin.

A composition for forming a coating of fibers on a target object by electrostatic spraying, comprising the following components (a), (b), (c) and (d):

(a) 1 mass % or more and 45 mass % or less of a polymer having a film-forming ability;
(b) 45 mass % to 95 mass % of one or more volatile substances selected from the group consisting of an alcohol and a ketone;
(c) a conductivity controlling agent to control the conductivity of the composition to 8 μS/cm or more and 300 μS/cm or less; and
(d) 0.2 mass % or more and 25 mass % or less of water.

12 Claims, 1 Drawing Sheet

(56) References Cited

FOREIGN PATENT DOCUMENTS

| WO | WO 01/12139 A1 | 2/2001 | |
|----|----|----|----|
| WO | WO 01/12335 A1 | 2/2001 | |
| WO | WO 2017/069079 A1 | 4/2017 | |
| WO | WO-2017082179 A1 * | 5/2017 | ........... B05B 12/084 |

OTHER PUBLICATIONS

International Search Report dated Jun. 26, 2018 in PCT/JP2018/016184 filed on Apr. 19, 2018.
Extended European Search Report dated Nov. 16, 2020 in European Patent Application No. 18787898.8, 12 pages.
"Air Touch Foundation" Database GNPD [Online] Mintel, anonymous: retreived from www.gnpd.com, Database Accesion No. 600036, XP055613371, Oct. 1, 2006, pp. 1-7.

* cited by examiner

Figure 1

Figure 2

COMPOSITION FOR FORMING COATING

FIELD OF THE INVENTION

The present invention relates to a composition for forming a coating by electrostatic spraying.

BACKGROUND OF THE INVENTION

Various methods for forming coatings by electrostatic spraying are known. For example, Patent Literature 1 discloses a process for treating skin comprising electrostatically spraying the skin with the compositions. The composition used in the method contains a liquid insulating material, a conductive material, a particulate powder material, and a thickener. As the composition, typically, a cosmetic product or a skincare composition containing a pigment is used. Specifically, a cosmetic foundation is used as the composition. That is, the invention disclosed in Patent Literature 1 primarily envisions decorating the skin by electrostatically spraying a cosmetic foundation for the cosmetic purpose.

Patent Literature 2 discloses disposable cartridges for use in electrostatic spraying devices for cosmetics. The electrostatic spraying device is a hand-held and self-contained type. This electrostatic spraying device is used for spraying a cosmetic foundation in the same manner as the Patent Literature 1 above.

(Patent Literature 1) JP-A-2006-104211
(Patent Literature 2) JP-A-2003-507165

SUMMARY OF THE INVENTION

The present invention relates to a composition for forming a coating of fibers on a target object by electrostatic spraying, comprising the following components (a), (b), (c) and (d):

(a) 1 mass % or more and 45 mass % or less of a polymer having a film-forming ability;

(b) 45 mass % to 95 mass % of one or more volatile substances selected from the group consisting of an alcohol and a ketone;

(c) a conductivity controlling agent to control the conductivity of the composition to 8 μS/cm or more and 300 μS/cm or less; and (d) 0.2 mass % or more and 25 mass % or less of water.

The present invention also relates to a method of forming a coating of fibers on a target surface using an electrostatic spraying device holdable by a human hand, comprising electrostatically spraying a composition comprising the following components (a), (b), (c) and (d) onto the target surface.

(a) 1 mass % or more and 45 mass % or less of a polymer having a film-forming ability;

(b) 45 mass % to 95 mass % of one or more volatile substances selected from the group consisting of an alcohol and a ketone;

(c) a conductivity controlling agent to control the conductivity of the composition to 8 μS/cm or more and 300 μS/cm or less; and (d) 0.2 mass % or more and 25 mass % or less of water.

BRIEF DESCRIPTION OF THE DRAWINGS

FIG. 1 is a schematic diagram showing a configuration of an electrostatic spraying device suitable for use in the present invention.

FIG. 2 is a schematic diagram showing the operation of an electrostatic spraying method using an electrostatic spraying device.

DETAILED DESCRIPTION OF THE INVENTION

When forming a coating with a fiber deposit on a target object, it is preferable to contain a small amount of water from the viewpoint of adhesivity to the object. However, it has been found that even if moisture imparting adhesion is used, when a coating is formed on a target object by using a hand-held type electrostatic spraying device, when moisture is present in the air, specifically, under high humidity conditions, fibers generated by electrostatic spraying fluctuate and are stacked on the object surface, fibers return to a hand holding the device or the device, or scatter around the object surface, so that a good coating cannot be formed on the object surface. In addition, when the spraying composition contains a large amount of water, a desired fiber may not be formed and a fibrous coating may not be formed.

Accordingly, the present invention relates to a spraying composition and a method for forming a coating, for the purpose of forming an excellent fibrous coating on a target surface even in high-humidity conditions in which a small amount of water is contained in the spraying composition.

As a result of extensive studies on components in the spraying composition, the present inventors have found that, if a composition containing a conductivity controlling agent for controlling the conductivity of the spraying composition in a certain range is used in addition to a polymer having a film-forming ability, volatile substances such as alcohols, and a small amount of water, even if the humidity is increased, the fibers formed by electrostatic spraying are accurately deposited on the target surface, and a coating composed of fibers having a high adhesivity is formed, thereby completing the present invention.

According to the present invention, even in high-humidity environments, fibers are prevented from returning to the electrostatic spraying device or the hand holding the device, fibers scattered to the periphery are also reduced, and a good fiber coating can be formed on the target surface. In addition, the obtained coating film is soft, and the adhesivity to the target surface is remarkably improved.

In the present invention, a composition for forming a fibrous coating on a target object by electrostatic spraying (hereinafter also referred to as a spraying composition) comprises the following components (a), (b), (c) and (d):

(a) 1 mass % or more and 45 mass % or less of a polymer having a film-forming ability;

(b) 45 mass % to 95 mass % of one or more volatile substances selected from the group consisting of an alcohol and a ketone;

(c) a conductivity controlling agent to control the conductivity of the composition to 8 μS/cm or more and 300 μS/cm or less; and (d) 0.2 mass % or more and 25 mass % or less of water.

The (a) polymer having a film-forming ability is generally a substance which can be dissolved in the volatile substance of component (b). Here, dissolving means a dispersed state at 20° C., and the dispersed state means a visually uniform state, preferably a visually transparent or translucent state.

As the polymer having a film-forming ability, a polymer suitable for the nature of the (b) volatile substance is used. Specifically, the polymer having a film-forming ability is a polymer which is soluble in component (b) and is poorly soluble in water. As used herein, the term "water-soluble polymer" means a polymer having a property in which, after weighing the polymer 1 g at 1 atm and 23° C., the polymer is immersed in 10 g of ion-exchanged water, and 0.5 g or more of the immersed polymer is dissolved in water after a lapse of 24 hours. In the present specification, the term "water-insoluble polymer" or "water-insoluble polymer" means a polymer having a property of not dissolving 0.05 g or more of the immersed polymer after weighing the polymer 1 g and then immersing it in 10 g of ion-exchanged water for 24 hours, in other words, a polymer having a property of dissolving less than 0.05 g.

Examples of the water-insoluble polymer having a film-forming ability include, a fully saponified polyvinyl alcohol which can be insolubilized after the formation of a coating, a partially saponified polyvinyl alcohol which can be crosslinked after the formation of a coating by using in combination with a crosslinking agent, an oxazoline-modified silicone such as a poly(N-propanoylethyleneimine)graft-dimethylsiloxane/γ-aminopropyl methylsiloxane copolymer, polyvinylacetaldiethyleminoacetate, Zein (a main component of corn protein), polyester, polylactic acid (PLA), an acrylic resin (e.g., a polyacrylonitrile resin, a polymethacrylic acid resin), a polystyrene resin, a polyvinyl butyral resin, a polyethylene terephthalate resin, a polybutylene terephthalate resin, a polyurethane resin, a polyamide resin, a polyimide resin, and a polyamide-imide resin. These water-insoluble polymers can be used alone or in combination of two or more. Among these water-insoluble polymers, it is preferable to use one or more selected from the group consisting of a fully saponified polyvinyl alcohol which can be insolubilized after the formation of a coating, a partially saponified polyvinyl alcohol which can be crosslinked after the formation of a coating by using in combination with a crosslinking agent, an acrylic resin such as polymethacrylic acid resin, a polyvinyl butyral resin, a polyurethane resin, polylactic acid (PLA), an oxazoline-modified silicone such as a poly(N-propanoylethyleneimine) graft-dimethylsiloxane/γ-aminopropylmethylsiloxane copolymer, polyvinylacetaldiethylaminoacetate, and Zein, and it is more preferable to use one or more selected from the group consisting of a polyvinyl butyral resin and a polyurethane resin.

The content of component (a) in the spraying composition is 1 mass % or more and 45 mass % or less, more preferably 5 mass % or more, more preferably 8 mass % or more, and preferably 10 mass % or more from the viewpoint of stably forming the coating even at higher humidity. The content of component (a) in the spraying composition is preferably 1 mass % or more and 45 mass % or less, more preferably 5 mass % or more and 45 mass % or less, more preferably 8 mass % or more and 45 mass % or less, more preferably 10 mass % or more and 40 mass % or less when component (a) contains one or more selected from the group consisting of a polyvinyl butyral resin and a polyurethane resin. The content of component (a) in the spraying composition is preferably 40 mass % or less. The content of component (a) in the spraying composition is preferably 1 mass % or more and 30 mass % or less, preferably 2 mass % or more and 25 mass % or less, more preferably 3 mass % or more and 20 mass % or less, and more preferably 5 mass % or more and 20 mass % or less, when component (a) contains a polyvinyl butyral resin. By containing component (a) in the spraying composition at this ratio, a fibrous coating can be formed stably and efficiently.

The (b) volatile substance is a substance which is volatile at 20° C. in the liquid state. In the spraying composition, component (b) is discharged from the nozzle tip toward the target object after sufficiently charging the spraying composition placed in the electric field, and when component (b) evaporates, the charge density of the spraying composition becomes excessive, and component (b) evaporates further while being further refined by Coulomb repulsion, and finally, component (b) is blended for the purpose of forming a coating containing fibers according to component (a). For this purpose, the volatile substance preferably has a vapor pressure at 20° C. of 0.01 kPa or more and 106.66 kPa or less, more preferably 0.13 kPa or more and 66.66 kPa or less, further more preferably 0.67 kPa or more and 40.00 kPa or less, and even more preferably 1.33 kPa or more and 40.00 kPa or less.

Among the (b) volatile substance, a monovalent chain aliphatic alcohol, a monovalent cyclic aliphatic alcohol, a monovalent aromatic alcohol, for example, are suitably used as an alcohol. Examples of the monovalent chain aliphatic alcohol include C1-C6 alcohols, example of the monovalent cyclic alcohol include C4-C6 cyclic alcohols, and examples of the monovalent aromatic alcohol include benzyl alcohol and phenethyl alcohol. Specific examples thereof include ethanol, isopropyl alcohol, butyl alcohol, phenylethyl alcohol, n-propanol, and n-pentanol. As these alcohols, one or more selected therefrom can be used.

Among the (b) volatile substances, examples of the ketone include C1-C4 dialkyl ketones such as acetone, methyl ethyl ketone, and methyl isobutyl ketone. These ketones can be used alone or in combination of two or more.

The (b) volatile substance is more preferably one or more selected from the group consisting of ethanol, isopropyl alcohol and butyl alcohol, more preferably one or more selected from the group consisting of ethanol and butyl alcohol, and more preferably a volatile substance containing at least ethanol from the viewpoint of the feel of the fiber.

The content of component (b) in the spraying composition is 45 mass % or more and 95 mass % or less, preferably 50 mass % or more, and more preferably 55 mass % or more. The content of component (b) in the spraying composition is preferably 92 mass % or less, and more preferably 89 mass % or less. The content of component (b) in the spraying composition is 50 mass % or more and 95 mass % or less, preferably 55 mass % or more and 94 mass % or less, more preferably 60 mass % or more and 93 mass % or less, and even more preferably 65 mass % or more and 92 mass % or less. By containing component (b) in the spraying composition at this ratio, when the electrostatic spraying method is performed, it is possible to sufficiently volatilize component (b) before the sprayed spraying composition reaches the target object or immediately after the spraying composition is attached to the object to form a fiber satisfactorily.

When component (a) contains a polyvinyl butyral resin, the content of component (b) is preferably 55 mass % or more and 92 mass % or less, more preferably 60 mass % or more and 90 mass % or less, and more preferably 65 mass % or more and 89 mass % or less.

The content ratio of component (b) to component (a), ((b)/(a)), in the spraying composition is 1 or more and 15 or less, more preferably 1.2 or more and 10 or less, and even more preferably 1.4 or more and 9 or less, from the viewpoint of sufficiently volatilizing component (b) and stably forming the coating of fibers when the electrostatic spraying method is performed.

The content ratio of the (b) ethanol to component (a), ((b)/(a)), in the spraying composition is 1 or more and 15 or less, more preferably 1.2 or more and 10 or less, and even more preferably 1.2 or more and 9 or less, from the standpoint of sufficiently volatilizing ethanol (b) and stably forming a coating of fibers when the electrostatic spraying method is performed.

The (c) conductivity controlling agent is a component that controls the conductivity of the spraying composition to 8 µS/cm or more and 300 µS/cm or less at 25° C. By controlling the conductivity of the spraying composition in this range, it is possible to stably form the coating of fibers on the application target surface by electrostatic spraying even under high humidity in which water is contained in the spraying composition.

The conductivity of the spraying composition is preferably 10 µS/cm or more, more preferably 15 µS/cm or more, and even more preferably 18 µS/cm or more from the viewpoint of stably forming the coating formed by the fibers. In addition, from the same viewpoint, the conductivity of the spraying composition is preferably 260 µS/cm or less, more preferably 220 µS/cm or less, and even more preferably 200 µS/cm or less. The conductivity of the spraying composition is preferably 10 µS/cm or more and 260 µS/cm or less, more preferably 15 µS/cm or more and 220 µS/cm or less, and even more preferably 18 µS/cm or more and 200 µS/cm or less. The conductivity of the compositions can be measured by an impedance-measuring device (SI1260, manufactured by Solartron Corporation) with a measuring terminal (SH-Z), 25° C., $\varphi$ 10 mm, and a distance of 1 mm.

As the (c) conductivity controlling agent, a water-soluble salt, an ethanol-soluble compound, and/or an ethanol-dispersible compound are preferable, an ionic compound or an acyl amino acid ester is more preferable from the viewpoint of conductivity improvement, and a betaine compound, anionic surfactant, anionic polymer, and an acyl amino acid ester are more preferable.

Examples of the ionic surfactant include a cationic surfactant, an anionic surfactant, and an amphoteric surfactants. As the cationic surfactant, a quaternary ammonium salt is preferable.

Examples of the quaternary ammonium salt include a tetraalkylammonium salt, a benzylalkylammonium salt, a benzyltrialkylammonium salt, an alkylbenzyldimethylammonium salt, a mono-long-chain alkyltrimethylammonium salt, and a di-long-chain alkyldimethylammonium salt. Specific examples thereof include cetyltrimethylammonium chloride, stearyltrimethylammonium chloride, behenyltrimethylammonium chloride, behenyldimethylhydroxyethylammonium chloride, distearyldiammonium chloride, stearyldimethylbenzylammonium chloride, distearyldimethylammonium chloride, dicetylmethylammonium chloride, cetyltriethylammonium methylsulfate, and benzalkonium chloride.

Examples of the anionic surfactant include an acyl amino acid salt, a fatty acid salt, an alkyl sulfate ester salt, an alkyl ether sulfate ester salt, an alkyl sulfonate salt, an alkyl phosphate ester salt, and an acyl amino acid salt is more preferable.

Examples of the acyl amino acid salt include an acyl glutamate, an acyl aspartate, an acyl sarcosine salt, an acyl taurine salt, an acyl methyl taurine salt, and an acyl alanine salt, and preferable examples of the salt include an alkali metal salt, an alkanolamine salt, and an ammonium salt. Examples of these acyl amino acid salts include sodium myristoyl glutamate, sodium myristoyl aspartate, sodium cocoyl glutamate, sodium lauroyl glutamate, sodium lauroyl aspartate, sodium lauroyl sarcosine, sodium palmitoyl sarcosine, triethanolamine acyl glutamate, and cocoyl alanine triethanolamine salt.

Examples of the amphoteric surfactant include a betaine-type and a sulfobetaine-type, and specific examples thereof include cocamidopropyl betaine, and cocamidopropyl hydroxy sultaine.

Examples of the acyl amino acid ester include an acyl amino acid (phytosteryl/octyldodecyl), and specific examples thereof include dilauroyl glutamate (phytosteryl/octyldodecyl).

Examples of the ionic polymer may include any one of an anionic polymer, a cationic polymer, and an amphoteric polymer. Examples of the anionic polymer include a homopolymer or a copolymer having (meth)acrylic acid units, such as acrylate/alkyl C1-18 acrylate/alkyl C1-8 acrylamide copolymer AMPs. Examples of the cationic polymer include a homopolymer or a copolymer having a primary to tertiary amino group or a quaternary ammonium group, such as ethyl acrylate/N-[3-(dimethylamino)propyl]amido/N-tert-butyl acrylamide/methacrylate-α-methylpoly(oxyethylene)-ω-yl-copolymer, a poly(N-propanoylethylimine)-graft-dimethylsiloxane/γ-aminopropylme thylsiloxane copolymer-monoethylsulfate salt. Examples of the amphoteric polymer include a homopolymer or copolymer having an alkyl betaine unit or a sulfobetaine unit, specifically an N-methylacryloyloxyethyl-N,N-dimethylammonium-α-N-methylcarboxybetaine/alkyl methacrylate copolymer.

Examples of the betaine compound include compounds in which three methyl groups are added to amino groups of amino acids, such as trimethylglycine, carnitine (vitamin Bt; 3-hydroxy-4-(trimethylammonio)butanoic acid ester), and acylated carnitine.

Component (c) is preferably one or more selected from the group consisting of a cationic surfactant, an anionic surfactant, an amphoteric surfactant, an acyl amino acid ester, an anionic polymer, a cationic polymer, an amphoteric polymer, and a betaine compound, more preferably a homopolymer or copolymer having a quaternary ammonium salt, an acyl amino acid salt, an acyl amino acid ester salt, a (meth)acrylic acid unit, a homopolymer or copolymer having primary to tertiary amino group(s), a homopolymer or a copolymer having quaternary ammonium group(s), a homopolymer or copolymer having alkylbetaine or sulfobetaine unit(s), and trimethylglycine.

The content of component (c) in the spraying composition is not limited as long as the conductivity of the composition is in the above range, but from the viewpoint of stably forming the coating even in high-humidity environments and from the viewpoint of preventing excessive increase in conductivity, 0.01 mass % or more and 10 mass % or less, more preferably 0.05 mass or more, more preferably 0.1 mass % or more, more preferably 8 mass % or less, even more preferably 6 mass % or less, even more preferably 2.5 mass % or less, and even more preferably 2 mass % or less.

When the polymer is contained, the content of component (c) is preferably 0.1 mass % or more, more preferably 0.5 mass % or more, preferably 15 mass % or less, and more preferably 10 mass % or less from the viewpoint of balancing the conductivity and the viscosity of the composition.

The content of component (c) in the spraying composition is not limited as long as the conductivity of the composition is in the above ranges, but is preferably 0.01 mass % to 15 mass %, more preferably 0.1 mass % to 10 mass % from the viewpoint of stably forming the coating even in high humidity environments, preventing excessive increase in conductivity, and suppressing increase in viscosity of the composition.

Component (d) is water. The content of water in the spraying composition is 0.2 mass % or more and 25 mass % or less, from the viewpoint of dissolving component (c) and thereby imparting conductivity, improving adhesivity of the coating formed by electrostatic spraying to the skin, improving formation of a stable coating, improving stability of spinning, and suppressing solidification and clogging of the raw material at the nozzle tip. The content of (d) water is preferably 0.25 mass % or more, more preferably 0.3 mass % or more. It is preferably 20 mass % or less, more preferably 15 mass % or less, and even more preferably 10 mass % or less. The content of (d) water in the spraying composition is preferably 0.25 mass % or more and 20 mass % or less, more preferably 0.3 mass % or more and 15 mass % or less, and even more preferably 0.3 mass % or more and 10 mass % or less.

The mass ratio of component (c) to component (d), ((c)/(d)), is preferably 0.01 or more, more preferably 0.02 or more, even more preferably 0.03 or more; preferably 6 or less, more preferably 5 or less, further more preferably 4 or less, from the viewpoint of imparting conductivity and improving coating formation ability and spinning stability. When a polymer is contained, ((c)/(d)), is preferably 40 or less, more preferably 30 or less.

The mass ratio of component (a) to component (d) in the spraying composition, ((a)/(d)), is preferably 0.4 or more, more preferably 0.5 or more, further more preferably 0.6 or more, even more preferably 1 or more, preferably 150 or less from the same viewpoint, preferably 50 or less from the same viewpoint, more preferably 45 or less, and even more preferably 40 or less from the same viewpoint when component (a) contains a polyvinyl butyral resin, from the viewpoint of compatibility between imparting conductivity and spraying performance.

The mass ratio of component (b) to component (d) in the spraying composition, ((b)/(d)), is preferably 3 or more, more preferably 4 or more, even more preferably 8 or more; preferably 300 or less, more preferably 280 or less, and even more preferably 270 or less from the viewpoint of improving the fiber forming property in a humid environment while dissolving or dispersing component (c) in the composition.

In addition, glycols may be included in the spraying composition. Examples of the glycol include ethylene glycol, propylene glycol, butylene glycol, diethylene glycol, dipropylene glycol, polypropylene glycol. From the viewpoint of suppressing plasticization of component (a) and stickiness of fibers by glycols, sufficiently volatilizing component (b) when the electrostatic spraying method is performed, and stably forming the coating of fibers, the content of glycol in the composition is preferably 10 mass % or less, more preferably 3 mass % or less, even more preferably 1 mass % or less, and substantially no content is preferable.

The spraying composition may contain only the above components (a) to (d), or may contain other component (s) in addition to components (a) to (d). Examples of the other components include, a polyol, an oil agent (a liquid oil, a solid fat), a plasticizer of (a) a polymer having a film-forming ability, a colored pigment, a constitutive pigment, a dye, a perfume, a repellent, an antioxidant, a stabilizer, a preservative, and various vitamins. When other components are contained in the spraying composition, the content ratio of the other components is preferably 0.1 mass % or more and 30 mass % or less, and more preferably 0.5 mass % or more and 20 mass % or less. The content of a powder such as a colored pigment, and a constitutive pigment in the spraying composition is preferably 1 mass % or less, more preferably 0.1 mass % or less, even more preferably 0.01 mass % or less, from the viewpoint of adhesivity of the coating, uniformity of the sprayed coating, and prevention of clogging, and it is also preferable that a powder is not contained except when unavoidably mixed in the composition.

The viscosity of the spraying composition at 25° C. is preferably from 2 to 3,000 mPa·s in view of stable formation of the fibrous coating, spinnability upon electrostatic spraying, drying of the fibers, reduction of the diameter of the fibers, and the like. The viscosity is preferably 5 mPa·s or more, more preferably 10 mPa·s or more, and even more preferably 30 mPa·s or more. The viscosity is preferably 2,000 mPa·s or less, more preferably 1, 500 mPa·s or less, further more preferably 1,000 mPa·s or less, and even more preferably 800 mPa·s or less. The viscosity range is preferably 2 mPa·s or more and 3,000 mPa·s or less, more preferably 5 mPa·s or more and 2,000 mPa·s or less, further more preferably 10 mPa·s or more and 1,500 mPa·s or less, even more preferably 30 mPa·s or more and 1,000 mPa·s or less, and even more preferably 30 mPa·s or more and 800 mPa·s or less. The viscosity of the spraying composition is measured at 25° C. using an E-type viscometer. As the E-type viscometer, for example, an E-type viscometer (VISCONIC EMD) manufactured by Tokyo Meters Co., Ltd. can be used. Then, the measurement conditions are 25° C., rotor No. 43 of the cone plate, and an appropriate rotation speed corresponding to the viscosity is selected; 5 rpm for the viscosity of 500 mPa·s or more, 10 rpm for the viscosity of 150 mPa·s or more and less than 500 mPa·s is 10 rpm, and 20 rpm for the viscosity of less than 150 mPa·s.

The relationship between the conductivity (Y [μS/cm]) of the spraying composition and the viscosity (X [mPa·s]) of 25° C. is such that Y/X is preferably 0.1 or more, more preferably 0.2 or more, further more preferably 0.3 or more; preferably 3.3 or less, more preferably 3 or less, further more preferably 2.5 or less, and even more preferably 2 or less, from the viewpoint of the spinning stability.

In the present invention, the spraying composition is electrostatically sprayed onto the target surface, leading to forming a coating of fibers. More specifically, the spraying composition is used in a method of forming a coating of fibers on a target surface to be applied using an electrostatic spraying device, preferably an electrostatic spraying device holdable by a human hand.

The target surface to be applied is a target surface on which a coating is directly formed, which is distinguished from a target surface for forming a coating for manufacturing a sheet product. For example, in forming a coating on human skin, nail, or the like by using an electrostatic spraying device with a human hand, unlike in manufacturing a sheet in a factory or the like, the humidity and the temperature are not under control. In the present invention, the target surface means a target surface on which a coating is formed by using a hand-held device holdable by a human hand, or at least which has an operation unit holdable by a human hand. The present invention enables to form an excellent coating over a rough surface which can be visually discernable or an uneven surface by using an electrostatic spraying device. Examples of the target surface include not only a metal surface, a plastic surface, a rubber surface, a ceramic surface, leather, artificial leather, but also a human skin surface, a human nail surface, a surface of various sites of a human body. In the present invention, a human skin surface and a human nail surface are more preferred, and a human skin surface is even more preferred.

The spraying composition may be sprayed directly onto the site to be coated, such as human skin, by electrostatic spraying.

Electrostatic spraying involves electrostatically spraying a spraying composition onto the skin using an electrostatic spraying device. An electrostatic spraying device basically includes a container containing the composition, a nozzle for discharging the composition, a supply device for supplying the composition contained in the container to the nozzle, and a power supply for applying a voltage to the nozzle.

Figure 1:
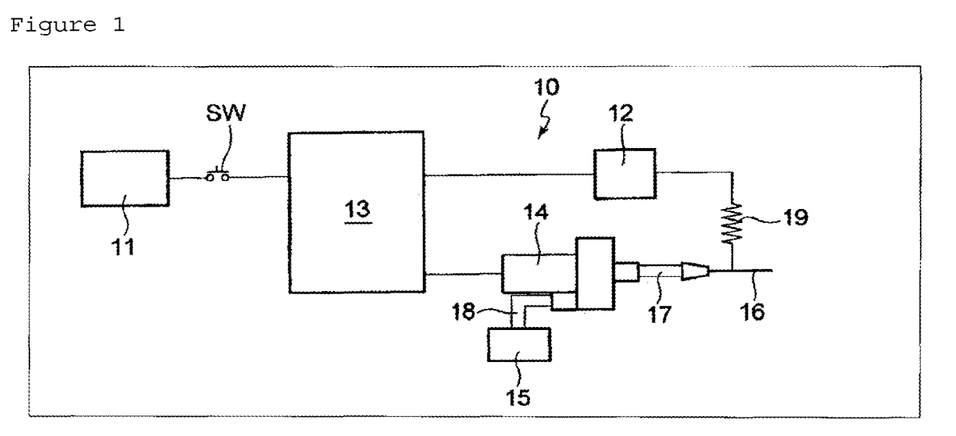

FIG. 1 is a schematic diagram showing a configuration of an electrostatic spraying device preferably used in the present invention. The electrostatic spraying device 10 shown in the figure includes a low voltage power supply 11. The low-voltage power supply 11 can generate a voltage of several volts or more and below 20 volts. For the purpose of enhancing the portability of the electrostatic spraying device 10, the low-voltage power supply 11 preferably comprises one or more batteries. Further, by using a battery as the low-voltage power supply 11, there is an advantage that replacement can be easily performed as necessary. Instead of the battery, an AC adapter or the like can be used as the low-voltage power supply 11.

The electrostatic spraying device 10 also includes a high-voltage power supply 12. The high-voltage power supply 12 is connected to the low-voltage power supply 11, and includes an electric circuit (not shown) for boosting a voltage generated by the low-voltage power supply 11 to a high voltage. The booster electric circuit is generally composed of a transformer, a capacitor, a semiconductor element, and the like.

The electrostatic spraying device 10 further comprises an auxiliary electrical circuit 13. The auxiliary electric circuit 13 is interposed between the low-voltage power supply 11 and the high-voltage power supply 12, and has a function of adjusting the voltage of the low-voltage power supply 11 to stably operate the high-voltage power supply 12. Further, the auxiliary electric circuit 13 has a function of controlling the number of revolutions of a motor provided in a microgear pump 14, which will be described later. By controlling the rotation speed of the motor, the supply amount of the spraying composition from the container 15 of the spraying composition described later to the microgear pump 14 is controlled. A switch SW is mounted between the auxiliary electric circuit 13 and the low-voltage power supply 11 so that the electrostatic spraying device 10 can be turned on and off by turning the switch SW on and off.

The electrostatic spraying device 10 further comprises a nozzle 16. The nozzle 16 is made of a conductive material such as metal or a non-conductive material such as plastic, rubber, ceramic, or the like, and has a shape capable of discharging the spraying composition from the tip thereof. A micro space through which the spraying composition flows is formed in the nozzle 16 along the longitudinal direction of the nozzle 16. The size of the cross section of the micro space is preferably 100 μm or more and 1,000 μm or less in terms of diameter, and preferably 300 μm or more and 1,400 μm or less.

The nozzle 16 communicates with the microgear pump 14 via a pipe 17. The pipe 17 may be conductive or non-conductive. The nozzle 16 is electrically connected to the high-voltage power supply 12. This makes it possible to apply a high voltage to the nozzle 16. In this case, in order to prevent an excessive current from flowing when a human body directly touches the nozzle 16, the nozzle 16 and the high-voltage power supply 12 are electrically connected via a current limiting resistor 19.

The microgear pump 14, which communicates with the nozzle 16 via a pipe 17, functions as a supply device for supplying the nozzle 16 with the spraying composition contained in the container 15. The microgear pump 14 is operated by receiving a power supply from the low-voltage power supply 11. The microgear pump 14 is configured to supply a predetermined amount of the spraying composition to the nozzle 16 under the control of the auxiliary electric circuit 13.

A container 15 is connected to the microgear pump 14 via a flexible pipe 18. Contained in the container 15 is the spraying composition. The container 15 preferably has a cartridge-type replaceable configuration.

Figure 2:
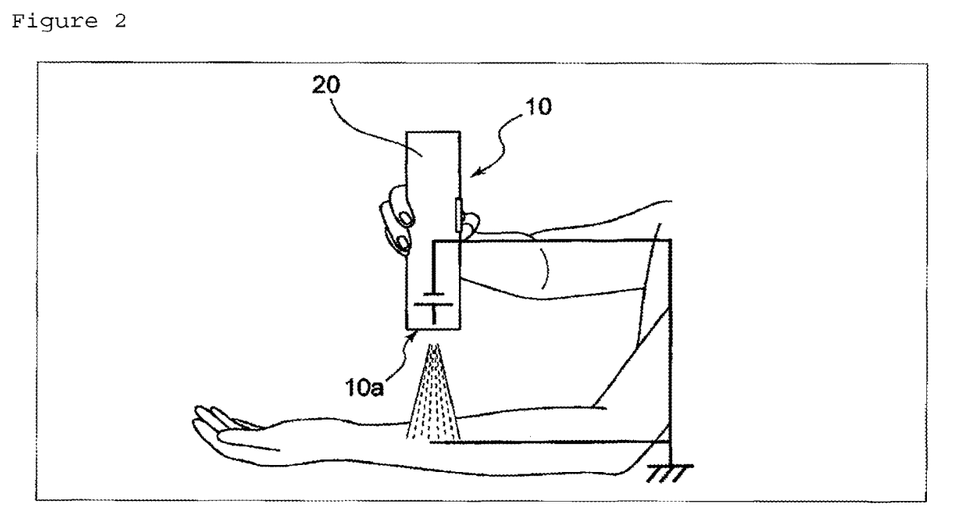

The electrostatic spraying device 10 having the above configuration can be used, for example, as shown in FIG. 2. FIG. 2 shows an electrostatic spraying device 10 of the hand-held type which is dimensioned holdable by one hand. The electrostatic spraying device 10 shown in the same figure contains all of the members of the configuration diagram shown in FIG. 1 in the cylindrical housing 20. A nozzle, not shown, is disposed at one longitudinal end 10a of the housing 20. The nozzle is disposed in the housing 20 such that the blowing direction of the composition coincides with the longitudinal direction of the housing 20 and is convex toward the skin side. By arranging the nozzle tip so as to be convex toward the skin in the longitudinal direction of the housing 20, the spraying composition hardly adheres to the housing, and the coating can be stably formed.

Next, a case where a coating is formed on the skin surface as an application target surface will be described.

When operating the electrostatic spraying device 10, the user, i.e., the person who forms the coating on the skin by electrostatic spraying, holds the device 10 by hand and directs one end 10a of the device 10, at which a nozzle, not shown, is located, to the application site where the electrostatic spraying is to be performed. In FIG. 2, one end 10a of the electrostatic spraying device 10 is shown pointing inside the user's forearm. In this state, the device 10 is switched on to perform the electrostatic spraying method. When the device 10 is powered on, an electric field is generated between the nozzle and the skin. In the embodiment shown in FIG. 2, a positive high voltage is applied to the nozzle and the skin becomes the negative electrode. When an electric field is generated between the nozzle and the skin, the spraying composition at the tip of the nozzle is polarized by electrostatic induction so that the tip portion becomes conical, and droplets of the spraying composition charged from the tip of the cone are discharged into the air toward the skin along the electric field. When component (b) as a solvent evaporates from the spraying composition discharged into the space and charged, the charge density on the surface of the spraying composition becomes excessive, and the space is swept by repeated refinement by Coulomb repulsion force to reach the skin. In this case, by appropriately adjusting the viscosity of the spraying composition, while being discharged into the space, a volatile substance as a solvent is volatilized from the droplets, the polymer of component (a) having a coating formation ability as a solute is solidified, the fiber is formed by stretching and deforming by a potential difference, and the fiber can be deposited at the application site. For example, increasing the viscosity of the spraying composition facilitates deposition of the composition in the form of fibers at the site of application. This forms a porous coating of a fiber deposit on the surface of the application site. A porous coating of such a fiber deposit can also be formed by adjusting the distance between the nozzle and the skin and the voltage applied to the nozzle.

During electrostatic spraying, a high potential difference occurs between the nozzle and the skin. However, since the impedance is very large, the current flowing through the human body is extremely small. For example, the inventors of the present the present invention have confirmed that the current flowing through the human body during the electrostatic spraying method is several orders of magnitude smaller than the current flowing through the human body due to static electricity generated in normal living conditions.

When a fiber deposit is formed by an electrostatic spray method, the thickness of the fiber is preferably 10 nm or more, more preferably 50 nm or more, when expressed as a circle equivalent diameter. The thickness is preferably 3,000 nm or less, and more preferably 1,000 nm or less. The thickness of the fiber can be measured by observing the fiber at a magnification of 10,000× by, for example, scanning electron microscopy (SEM) observation, removing defects (clumps of fibers, crossing portions of fibers, and droplets) from the two-dimensional image, arbitrarily selecting 10 fibers, drawing a line orthogonal to the longitudinal direction of the fiber, and directly reading the fiber diameter.

According to the electrostatic spraying method, the spraying composition is charged and sprayed, and when the humidity is high, the spraying composition is affected by moisture in the atmosphere, but by including component (c) the conductivity control agent, the spraying composition can be made less susceptible to this effect. This is considered to increase the conductivity by dissolving or dispersing at least a part of the conductivity controlling agent by component (d) water contained in the spraying composition and ionizing by containing component (c) conductivity controlling agent, thereby making it less susceptible to the influence on the humidity. The present invention enables to prevent the influence from moisture while allowing moisture to be present on the surfaces of the fibers immediately after spraying because of the adhesivity of the fibers to the target object. The surface of a fiber means a surface, or a portion of a surface, between fibers. In addition, when the moisture-bearing coating is formed on the fibers constituting the coating in this manner, the adhesivity with the skin increases, the coating tends to become transparent, and the natural appearance is approached. Further, since the durability of the adhesion is increased, it is effective for the moisturization of the skin or the improvement of the condition of the skin. The effect of the adhesiveness is further enhanced by a liquid agent applied before or after spraying, which will be described later.

When the skin contains sweat, sebum, or the like, moisture or oil is compounded in the fibers or between the fibers, so that the fibers tend to swell or plasticize. For example, when the same composition is electrostatically sprayed onto a metal surface containing no moisture or oil and on a skin surface containing moisture or oil, for example, on the palm of the hand, for 5 seconds to prepare a thin coating, when a change in the fiber diameter is observed over time, the fiber electrostatically sprayed onto the skin surface becomes larger in diameter over time by swelling than the fiber electrostatically sprayed on the metal surface. Thus, the fiber-containing coating formed by electrostatic spraying is plasticized by the oil and moisture in the skin to become softer, thereby improving the ability of the fiber itself to follow the texture of the skin, and the moisture bleeds out from the fiber and exists between the fiber surface and the fiber, whereby the fiber-containing coating becomes translucent or transparent, thereby imparting a natural appearance. Where the object to be coated is skin containing sweat, sebum, or the like, the fiber diameter due to swelling satisfies the following equation (1):

(Fiber diameter 30 seconds after spinning on the skin)>(Fiber diameter 30 seconds after spinning on the metal plate) (1)

The contents of components (a), (c) and (d) contained in the spraying composition are measured as follows. Since the (b) volatile substance (b) does not exist in the formed coating or volatilizes even if it exists, the formed coating is measured in a state in which only component (a), component (c), and component (d) are contained, and the content thereof is measured as follows.

<Determination of the Content of Component (a), Component (c) and Component (d) of the Spraying Composition>

Separate identification by liquid chromatography (HPLC) and identification by infrared spectrophotometer (IR) are available in solution. Since the liquid chromatograph elutes from a component having a large molecular weight, the composition can be identified by predicting the molecular weight or by determining the elution position of component. It is also possible to assign and identify functional groups from individual absorbers by IR analysis, and it is generally possible to identify them by comparing IR charts of components with standard charts of commercial additives.

<Determination of the Content of Component (a) and Component (c) in the Formed Coating>

A solvent capable of dissolving the coating is searched for, and after dissolving the coating in the solvent, separation/identification by a liquid chromatograph (HPLC) or identification by an infrared spectrophotometer (IR) is performed.

In the method for producing the spraying composition, the mixture solution containing all components may be stirred, but it is preferable that Step 1 of stirring the mixed solution 1 containing components other than component (a) be followed by Step 2 of adding component (a) and stirring and mixing. These Steps 1 and 2 are preferably performed at a normal temperature of from 10° C. to 30° C.

The fiber forming the coating is a continuous fiber of infinite length in principle of production, but it is preferable that the fiber has a length of at least 100 times or more of the thickness of the fiber. In the present specification, a fiber having a length of 100 times or more of the thickness of the fiber is defined as a “continuous fiber”. The coating produced by the electrostatic spraying method is preferably a porous discontinuous coating composed of a deposit of continuous fibers. Such a form of coating not only can be handled as a single sheet as an aggregate, but also has the advantage that it has a very soft feature, and it is difficult to be separated even when a shearing force is applied to it, and it is excellent in the following property to the movement of the body. In addition, advantageously, the coating can be easily completely removed. In contrast, a continuous coating having no pores is not easy to peel off and has a low sweat dissipation property, so that there is a fear that the skin will become blistered. In addition, it is difficult to completely remove the porous discontinuous coating formed of the aggregate of particles without damaging the skin, for example, an operation of applying friction or the like to the entire coating is necessary in order to completely remove the coating.

In the electrostatic spraying step using the electrostatic spraying device 10, the spraying composition which has been electrostatically sprayed into a fibrous state, directly reaches the skin in a state in which component (a) and component (c) are charged while component (b) evaporates.

Since the skin is also charged as described hereinbefore, the fibers adhere to the skin in the form of a single film by electrostatic forces. Since fine unevenness such as texture are formed on the skin surface, the fibers are more closely adhered to the skin surface in the form of a single film in combination with the anchoring effect due to the unevenness. When the electrostatic spraying is completed in this manner, the power of the electrostatic spraying device 10 is turned off. This disappears the electric field between the nozzle and the skin, and an electric charged is fixed on the skin surface. As a result, the adhesivity of the coating in the form of a single film is further developed, the coating is hard to peel off from the edge during wearing, and so coating durability during use is improved. It is also noted that since the fiber constituting the coating contains moisture, not only an excellent moisturizing effect and a softening effect of the coating can be obtained, but also the coating can be sufficiently adhered to the skin. The reason for this is considered to be that the fibers per se are softened by the plasticizing effect due to the presence of moisture in the fibers or between the fibers, to enhance the followability to the fine uneven surface, and that the moisture bleeds out to the fiber surface to cause liquid crosslinking the fibers and the skin. Furthermore, since the coating has a moisture-bearing coating in which moisture is present between fibers constituting the coating or on the fiber surface, the fibers constituting the coating are hard to reflect light and so the coating tends to look transparent, and the skin can be covered in a natural appearance. These effects are further enhanced by liquid application before or after the spraying as described hereafter.

The distance between the nozzle and the skin depends on the voltage applied to the nozzle, but is preferably 10 mm or more, more preferably 20 mm or more, more preferably 40 mm or more, more preferably 160 mm or less, more preferably 150 mm or less, and even more preferably 120 mm or less from the viewpoint of improving the coating forming property. The distance between the nozzle and the skin can be measured by a commonly used non-contact sensor or the like.

Whether or not the coating formed by the electrostatic spraying method is porous, the basis weight of the coating is preferably 0.1 g/m$^2$ or more, more preferably 1 g/m$^2$ or more. The basis weight of the formed coating is preferably 50 g/m$^2$ or less, and more preferably 40 g/m$^2$ or less. The basis weight of the formed coating is preferably greater than or equal to 0.1 g/m$^2$ and less than or equal to 50 g/m$^2$, and more preferably greater than or equal to 1 g/m$^2$ and less than or equal to 40 g/m$^2$. By setting the basis weight of the coating in this manner, the coating adhesivity can be improved.

The electrostatic spraying step of forming a coating by electrostatically spraying the composition directly onto the skin means a step of electrostatically spraying the skin to form a coating. The process of electrostatically spraying the composition to a location other than the skin to produce a sheet of fibers and applying the sheet to the skin differs from the electrostatically spraying process described above.

In the present invention, prior to or after the electrostatic spraying process for forming a coating on the skin by electrostatic spraying as described above, a liquid application process may be performed in which a liquid agent containing one or more selected from a liquid polyol at 20° C. and a liquid oil at 20° C. is applied to the skin by means other than electrostatic spraying. By performing the liquid agent application step, the coating formed by the electrostatic spraying step becomes more familiar to the application site, and the coating can be highly adhered to the skin and can be made more transparent. For example, a step is less likely to occur between the edge of the coating and the skin, thereby improving the adhesivity between the coating and the skin. As a result, peeling, tear, or the like of the coating is less likely to occur. In a more preferable embodiment, when the coating is a porous coating composed of a fiber deposit, the adhesivity with the skin is high despite the high porosity, and a large capillary force is apt to occur. Further, when the fibers are fine, it is easy to make the porous coating have a high specific surface area.

In particular, after forming a porous coating composed of a fiber deposit in an electrostatic spraying process, a liquid coating process is performed by means other than electrostatic spraying to form a coating in which the liquid agent is present between the fibers forming the porous coating and/or on the surface of the fibers. This improves the adhesivity of the coating and maintains or improves the transparency of the coating for visual inspection. In particular, when the coating is colorless and transparent or colored and transparent, the coating becomes more difficult to visually recognize, so that the coating can appear like natural skin. In addition, when the coating is colored and transparent, the coating has a transparent feeling, so that it can appear as a part of the skin.

Examples of the oil in a liquid state at 20° C. include, a straight or branched hydrocarbon oil such as liquid paraffin, light isoparaffin, liquid isoparaffin, squalane, squalene; an ester oil such as a monoalcohol fatty acid ester, a polyvalent alcohol fatty acid ester, a triglyceryl fatty acid ester (triglyceride); a silicone oil such as dimethylpolysiloxane, dimethylcyclopolysiloxane, methylphenylpolysiloxane, methylhydrogenpolysiloxane, a high alcohol modified organopolysiloxane; and one or more selected from these can be used in combination. Among these, one or more selected from the group consisting of a hydrocarbon oil and an ester oil are preferable from the viewpoint of smoothness upon application and the like. In addition, a vegetable oil or an animal oil including these hydrocarbon oils and ester oils can also be used.

Examples of the hydrocarbon oil include liquid paraffin, squalane, squalene, n-octane, n-heptane, cyclohexane, wherein isoparaffin, liquid isoparaffin, and liquid paraffin and squalane are preferable from the viewpoint of impression from use. In addition, from the viewpoint of adhering the electrostatically sprayed coating film to the skin, the viscosity of the hydrocarbon oil at 30° C. is preferably 10 mPa·s or more, more preferably 30 mPa·s or more. From this viewpoint, the total content of isododecane, isohexadecane, hydrogenated polyisobutene having viscosities of less than 10 mPa·s at 30° C. is preferably 10 mass % or less, more preferably 5 mass % or less, even more preferably 1 mass % or less, even more preferably 0.5 mass % or less, and may not be contained.

Similarly, from the standpoint of adhering the electrostatic sprayed coating to the skin, the viscosity of the ester oil and the silicone oil at 30° C. is preferably 10 mPa·s or more, more preferably 30 mPa·s or more.

The viscosity here is measured at 30° C. with a BM-type viscometer (manufactured by Tokimek Corporation, measurement conditions: Rotor No. 1, 60 rpm, 1 minute).

From the same viewpoint, the total content of the ether oil such as cetyl-1,3-dimethylbutyl ether, dicapryl ether, dilauryl ether, diisostearyl ether in the liquid agent is preferably 10 mass % or less, more preferably 5 mass % or less, and even more preferably 1 mass % or less.

Examples of the ester oil include an ester consisting of a linear or branched chain fatty acid and a linear or branched chain alcohol or a polyvalent alcohol. Specific examples thereof include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethyleneglycol di(2-ethylhexanoate), dipentaerythritol fatty acid ester, N-alkylglycol monoisostearate, neopentylglycol dicaprate, diisostearyl malate, glyceryl di(2-heptylundecanoate), trimethylolpropane tri(2-ethylhexanoate), trimethylolpropane triisostearate, pentaerythritol tetra(2-ethylhexanoate), glyceryl tri(2-ethylhexanoate), trimethylolpropane triisostearate, cetyl 2-ethylhexanoate, 2-ethylhexyl palmitate, diethylhexyl naphthalenedicarboxylate, (C12-15)alkyl benzoate, cetearyl isononanoate, caprylic/capric triglyceride, dicaprylic/capric butyleneglycol, glyceryl trilaurate, glyceryltrimyristate, glyceryltripalmitate, glyceryltriisostearate, glyceryl tri(2-heptylundecanoate), glyceryl tribehenate, glyceryl tricocoate, castor oil fatty acid methyl ester, oleyl oleate, 2-heptylundecyl palmitate, diisobutyl adipate, N-lauryol-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di(2-ethylhexyl) succinate, triethyl citrate, 2-ethylhexyl para-methoxycinnamate, tripropylene glycol dipivalate, and the like.

Among these, from the viewpoint of adhering the coating to the skin, at least one selected from the group consisting of octyldodecyl myristate, myristyl myristate, isocetylstearate, isocetylisostearate, cetearyl isonanoate, diisobutyl adipate, di-2-ethylhexyl sebacate, isopropyl myristate, isopropyl palmitate, diisostearyl malate, neopentylglycoldicaprate, (C12-15) alkyl benzoate, and caprylic/capric triglyceride, is preferable. At least one selected from the group consisting of isopropyl myristate, isopropyl palmitate, diisostearyl malate, neopentylglycol dicaprate, (C12-15)alkyl benzoate, and caprylic/capric triglyceride is more preferable. It is further preferable to contain one or more selected from neopentylglycol dicaprate, (C12-15)alkyl benzoate, caprylic/capric triglyceride and isopropyl myristate.

Examples of the triglyceride preferably include a triglyceryl fatty acid ester, which is contained in, for example, an olive oil, a jojoba oil, a macademia nut oil, a medform oil, a castor oil, a red flower oil, a sunflower oil, an avocado oil, a canola oil, a ginseng oil, a rice germ oil, a rice bran oil and the like.

Examples of the higher alcohol include a liquid higher alcohol having 12 to 20 carbon atoms, specifically isostearyl alcohol, oleyl alcohol.

Examples of the silicone oil include dimethylpolysiloxane, dimethylcyclopolysiloxane, methylphenylpolysiloxane, methylhydrogenpolysiloxane, higher alcohol modified organopolysiloxane.

The kinematic viscosity of the silicone oil at 25° C. is preferably 3 mm$^2$ per second, more preferably 4 mm$^2$ per second, more preferably 5 mm$^2$ per second or more, more preferably 30 mm$^2$ per second or less, more preferably 20 mm$^2$ per second or less, and still more preferably 10 mm$^2$ per second or less from the viewpoint of adhering the electrostatically sprayed coating to the skin.

Among these, it is preferable to contain dimethylpolysiloxane from the viewpoint of adhering the electrostatically sprayed coating to the skin.

The content of the oil in a liquid state at 20° C. is preferably 0.1 mass % or more, more preferably 0.5 mass % or more, and even more preferably 5 mass % or more. It is preferably 100 mass % or less. The content of the oil in the liquid at 20° C. is preferably 0.1 mass % or more and 100 mass % or less, more preferably 0.5 mass % or more and 100 mass % or less.

Examples of the polyol liquid at 20° C. used in the liquid agent include alkylene glycols such as ethylene glycol, propylene glycol, 1,3-propanediol, and 1,3-butanediol; dialkylene glycols such as diethylene glycol and dipropylene glycol; polyalkylene glycols such as polyethylene glycol and polypropylene glycol having a weight average molecular weight of 2,000 or less; glycerins such as glycerin, diglycerin, and triglycerin. Among these, ethylene glycol, propylene glycol, 1,3-butanediol, dipropylene glycol, polyethylene glycol having a weight average molecular weight of 2,000 or less, glycerin, and diglycerin are preferable from the viewpoint of smoothness upon application, and further propylene glycol, 1,3-butanediol, dipropylene glycol, and glycerin are more preferable, and propylene glycol, 1,3-butanediol, and glycerin are more preferable.

The liquid agent preferably has a viscosity at 25° C. of 5,000 mPa·s or less from the viewpoint of improving the adhesivity between the coating formed by the electrostatic spraying method and the application site. The method of measuring the viscosity of the liquid is as described above.

The solution may be applied to the skin by any means other than electrostatic spraying, and various methods can be used. For example, by applying a liquid agent to the skin by a method such as dropping or sprinkling, and by providing a step of spreading the liquid agent, it becomes possible to conform to the skin or the coating, and a thin layer of the liquid agent can be formed. The step of spreading the solution may employ, for example, a method such as rubbing using a finger of the user or a tool such as an applicator. The solution may be simply dropped or sprinkled, but providing the spreading step enables to conform the solution to the skin or the coating, thereby sufficiently improving the adhesivity of the coating. Alternatively, the solution can be sprayed onto the skin to form a thin layer of the solution. In this case, separate spreading is not particularly necessary, but spreading after spraying is not hindered. When a liquid is applied after the coating formation, a sufficient amount of the liquid is applied to the skin, and the excess liquid can be removed by subjecting a sheet material into contact with the liquid-applied area, thereby the excess liquid can be removed.

The amount of the liquid agent to be applied to the skin may be an amount necessary and sufficient to improve the adhesivity between the skin and the coating. When a liquid oil is contained in the liquid agent, from the viewpoint of ensuring the adhesivity between the skin and the coating, the amount of the liquid agent to be applied to the skin is such that the basis weight of the liquid oil is preferably 0.1 g/m$^2$ or more, more preferably 0.2 g/m$^2$ or more, preferably 40 g/m$^2$ or less, and more preferably 35 g/m$^2$ or less. For example, the amount of the liquid to be applied to the skin is such that the basis weight of the liquid oil is preferably 0.1 g/m$^2$ or more and 40 g/m$^2$ or less, more preferably 0.2 g/m$^2$ or more and 35 g/m$^2$ or less.

In addition, the amount of the solution to be applied to the skin or the coating is preferably 5 g/m$^2$ or more, more preferably 10 g/m$^2$ or more, more preferably 15 g/m$^2$ or more, preferably 50 g/m$^2$ or less, and more preferably 45 g/m$^2$ or less from the viewpoint of improving the adhesivity between the skin and the coating and improving the transparency.

Although the present invention has been described above with reference to its preferred embodiment, the present invention is not limited to the embodiments described above. For example, in the embodiment described above, a person who wants to form a coating on his or her own skin holds the electrostatic spraying device 10 and generates an electric field between the device 10 and his or her skin, but as long as an electric field is generated between the two, it is not necessary for him or her to hold the electrostatic spraying device 10.

With respect to the embodiments described above, the present invention further disclose the following compositions and methods.

<1> A composition for forming a coating of fibers on a target object by electrostatic spraying, the composition comprising the following components (a), (b), (c) and (d):
 (a) 1 mass % or more and 45 mass % or less of a polymer having a film-forming ability;
 (b) 45 mass % to 95 mass % of one or more volatile substances selected from the group consisting of an alcohol and a ketone;
 (c) a conductivity controlling agent to control the conductivity of the composition to 8 µS/cm or more and 300 µS/cm or less; and
 (d) 0.2 mass % or more and 25 mass % or less of water.

<2> The composition according to <1>, wherein the (a) polymer having a film-forming ability is a substance that can be dissolved in the (b) volatile substance and is a water-insoluble polymer.

<3> The composition according to <1> or <2>, wherein the polymer having a film-forming ability is one or more selected from the group consisting of a fully saponified polyvinyl alcohol which can be insolubilized after the coating formation, a partially saponified polyvinyl alcohol which can be crosslinked by using in combination with a crosslinking agent after the coating formation, an oxazoline-modified silicone such as poly(N-propanoylethyleneimine) graft-dimethylsiloxane/γ-aminopropylmethylsiloxane copolymer, a polyvinylacetaldiethylaminoacetate, Zein, a polyester, a polylactic acid, an acrylic resin (e.g., a polyacrylonitrile resin, a polymethacrylic acid resin), a polystyrene resin, a polyvinyl butyral resin, a polyethylene terephthalate resin, a polyurethane resin, a polyamide resin, a polyimide resin and a polyamide-imide resin; more preferably one or more selected from the group consisting of a fully saponified polyvinyl alcohol which can be insolubilized after the coating formation, a partially saponified polyvinyl alcohol which can be crosslinked by using in combination with a crosslinking agent after the coating formation, an acrylic resin (e.g., a polymethacrylic acid resin), a polyvinyl butyral resin, a polyurethane resin, polylactic acid, an oxazoline-modified silicone such as poly(N-propanoylethyleneimine) graft-dimethylsiloxane/γ-aminopropylmethylsiloxane copolymer, polyvinylacetaldiethylaminoacetate, and Zein; even more preferably one or more water-insoluble polymer selected from the group consisting of a polyvinyl butyral resin and a polyurethane resin.

<4> The composition according to any one of <1> to <3>, wherein the content of component (a) in the composition is preferably 5 mass % or more, more preferably 8 mass % or more, further more preferably 10 mass % or more; preferably 45 mass % or less, more preferably 40 mass % or less; preferably 5 mass % or more and 45 mass % or less, more preferably 8 mass % or more and 40 mass % or less, and more preferably 10 mass % or more and 40 mass % or less.

<5> The composition according to any one of <1> to <4>, wherein the (b) volatile substance has a vapor pressure at 20° C. of 0.01 kPa or more and 106.66 kPa or less, more preferably 0.13 kPa or more and 66.66 kPa or less, further more preferably 0.67 kPa or more and 40.00 kPa or less, and even more preferably 1.33 kPa or more and 40.00 kPa or less.

<6> The composition according to any one of <1> to <5>, wherein the (b) volatile substance is an alcohol, and one or more selected from the group consisting of monovalent chain aliphatic alcohol, monovalent cyclic aliphatic alcohol, and a monovalent aromatic alcohol are preferable as the alcohol, and one or more selected from the group consisting of ethanol, isopropyl alcohol, butyl alcohol, phenylethyl alcohol, propanol, and pentanol are more preferable as the alcohol.

<7> The composition according to any one of <1> to <6>, wherein the (b) volatile substance is one or more selected from the group consisting of ethanol, isopropyl alcohol, butyl alcohol, and water, more preferably one or two selected from the group consisting of ethanol and butyl alcohol, and even more preferably a volatile substance comprising at least ethanol.

<8> The composition according to any one of <1> to <7>, wherein the content of component (b) in the composition is preferably 50 mass % or more, more preferably 55 mass % or more; preferably 92 mass % or less, more preferably 89 mass % or less; preferably 50 mass % or more and 92 mass % or less, and more preferably 55 mass % or more and 89 mass % or less.

<9> The composition according to any one of <1> to <8>, wherein the conductivity of the composition by the (c) conductivity controlling agent is preferably 10 µS/cm or more, more preferably 15 µS/cm or more, even more preferably 18 µS/cm or more; preferably 260 µS/cm or less, more preferably 220 µS/cm or less, even more preferably 200 µS/cm or less; preferably 10 µS/cm or more and 260 µS/cm or less, more preferably 15 µS/cm or more and 220 µS/cm or less, and even more preferably 18 µS/cm or more and 200 µS/cm or less.

<10> The composition according to anyone of <1> to <9>, wherein component (c) is preferably one or more selected from the group consisting of a water-soluble salt, an ethanol-soluble compound and an ethanol-dispersible compound, more preferably one or more selected from the group consisting of anionic compound and an acyl amino acid ester, further more preferably one or more selected from the group consisting of a cationic surfactant, an anionic surfactant, an amphoteric surfactant, an acyl amino acid ester, an anionic polymer, a cationic polymer and a betaine compound, even more preferably one or more selected from the group consisting of a quaternary ammonium salt, an acyl amino acid salt, an acyl amino acid ester, a homopolymer or copolymer having a (meth)acrylic acid unit, a homopolymer or copolymer having a primary to tertiary amino acid group, a homopolymer or copolymer having a quaternary ammonium group, a homopolymer or copolymer having an alkyl betaine unit or a sulfobetaine unit, and trimethylglycine.

<11> The composition according to any one of <1> to <10>, wherein the content of component (c) in the composition is preferably 0.01 mass % or more and 15 mass % or less, more preferably 0.05 mass % or more, preferably 0.1 mass % or more, more preferably 10 mass % or less, and preferably 0.1 mass % or more and 10 mass % or less.

<12> The composition according to anyone of <1> to <11>, wherein the content of the (d) water in the composition is preferably 0.2 mass % or more, more preferably 0.25 mass % or more, even more preferably 0.4 mass % or more; preferably 25 mass % or less, more preferably 20 mass % or less, furthermore preferably 15 mass % or less, even more preferably 10 mass % or less; preferably 0.25 mass % or more and 20 mass % or less, more preferably 0.3 mass % or more and 15 mass % or less, and even more preferably 0.3 mass % or more and 10 mass % or less.

<13> The composition according to any one of <1> to <12>, wherein the mass ratio of component (c) and component (d), ((c)/(d)), is preferably 0.01 or more, more preferably 0.02 or more, even more preferably 0.03 or more; preferably 150 or less, more preferably 6 or less, further more preferably 5 or less, even more preferably 4 or less; preferably from 0.01 to 40, and more preferably from 0.3 to 30.

<14> The composition according to any one of <1> to <13>, further comprises other components selected from the group consisting of a polyol, an oil agent, a plasticizer of the (a) polymer having a film-forming ability, a colored pigment, a constitutional pigment, a dye, a perfume, a repellent, an antioxidant, a stabilizer, a preservative, and various vitamins, and the content of the other components is preferably 0.1 mass % or more and 30 mass or less, and more preferably 0.5 mass % and 20% or less.

<15> The composition according to any one of <1> to <14>, wherein the content of the powder in the composition is preferably 1 mass % or less, more preferably 0.1 mass % or less, further more preferably 0.01 mass % or less, and it is preferable not to contain a powder except when inevitably mixed in.

<16> The composition according to any one of <1> to <15>, the viscosity of the composition at 25° C. is preferably from 2 to 3,000 mPa·s; preferably 5 mPa·s or more, more preferably 10 mPa·s or more, even more preferably 30 mPa·s or more; preferably 2,000 mPa·s or less, more preferably 1,500 mPa·s or less, further more preferably 1,000 mPa·s or less, even more preferably 800 mPa·s or less; preferably 2 mPa·s or more and 3,000 mPa·s or less, more preferably 5 mPa·s or more and 2,000 mPa·s or less, further more preferably 10 mPa·s and 1,500 mPa·s or less, even more preferably 30 mPa·s or more and 1,000 mPa·s or less.

<17> The composition according to any one of <1> to <16>, wherein the relationship between the conductivity (Y [μS/cm]) and the viscosity (X) at 25° C. is 0.1 or more, 0.2 or more, 0.3 or more, 3 or less, 3 or less, 2.5 or less, and 2 or less.

<18> The composition according to any one of <1> to <17>, wherein the target surface is a metal surface, a plastic surface, a rubber surface, a ceramic surface, leather, artificial leather, or a skin surface, and preferably a skin surface.

<19> The composition according to any one of <1> to <18>, wherein the electrostatic spraying is performed by using an electrostatic spraying device having a container containing the composition, a nozzle discharging the composition therefrom, a supply device supplying the composition contained in the container to the nozzle, and a power source applying a voltage to the nozzle.

<20> The composition according to any one of <1> to <19>, wherein the electrostatic spraying is performed by using an electrostatic spraying device,
    the electrostatic spraying device contains a nozzle,
    the nozzle is made of a conductive material such as metal or a non-conductive material such as plastic, rubber, ceramic, and the nozzle has a shape capable of discharging the composition from the tip thereof.

<21> The composition according to any one of <1> to <20>, wherein the electrostatic spraying is performed by using an electrostatic spraying device,
    the electrostatic spraying device includes a nozzle and a housing,
    the nozzle is disposed at one longitudinal end of the housing,
    the nozzle is disposed in the housing such that the blowing direction of the composition coincides with the longitudinal direction of the housing and is convex toward the skin side.

<22> The composition according to any one of <1> to <21>, wherein the sprayed composition is volatilized from droplets of a volatile substance as a solvent to solidify a polymer having a film-forming ability as a solute, and a fiber is formed by elongation deformation by a potential difference.

<23> The composition according to any one of <1> to <22>, wherein the electrostatic spraying is performed by using an electrostatic spraying device,
    the electrostatic spraying device contains a nozzle,
    the distance between the nozzle and the skin is 10 mm or more and 160 mm or less, preferably 20 mm or more and 150 mm or less, more preferably 40 mm or more and 120 mm or less.

<24> The composition according to any one of <1> to <23>, wherein the basis weight of the coating formed by the electrostatic spraying is preferably 0.1 g/m$^2$ or more, more preferably 1 g/m$^2$ or more; 30 g/m$^2$ or less, more preferably 20 g/m$^2$ or less; preferably 0.1 g/m$^2$ or more and 30 g/m$^2$ or less, more preferably 1 g/m$^2$ or more and 20 g/m$^2$ or less.

<25> The composition according to any one of <1> to <24>, wherein the content of glycol in the composition is preferably 10 mass % or less, more preferably 3 mass % or less, and even more preferably 1 mass % or less.

<26> The composition according to any one of <1> to <25>, wherein component (b) is a volatile substance comprising at least ethanol, and component (a) is one or more selected from the group consisting of a polyvinyl butyral resin and a polyurethane resin.

<27> The composition according to any one of <1> to <26>, wherein component (b) is a volatile substance comprising at least ethanol, and the content of glycol is 1 mass % or less.

<28> The composition according to any one of <1> to <27>, wherein component (b) is a volatile substance comprising at least ethanol, the content of ethanol in the volatile substance is 50 mass % or more and 100 mass %, and the content of powder in the composition is 1 mass % or less.

<29> The composition according to any one of <1> to <28>, wherein the content of component (a) is 10 mass % or more and 40 mass % or less, the content of component (b) is 55 mass % or more and 89 mass % or less, and the mass ratio of the content of component (b) to the content of component (a), ((b)/(a)), is from 1.4 to 9.

<30> The composition according to any one of <1> to <29>, wherein the content of component (d) is 0.3 mass % or more and 10 mass % or less, and the mass ratio of the content of component (a) to the content of component (d), ((a)/(d)), is 1 or more and 150 or less.

<31> The composition according to any one of <1> to <30>, wherein the conductivity of the composition by the (c) conductivity controlling agent is 10 μS/cm or more and 300 μS/cm or less.

<32> The composition according to any one of <1> to <31>, wherein the relationship between the conductivity (Y [μS/cm]) of the composition and the viscosity (X [mPa·s]) of the composition at 25° C., (Y/X), is 0.1 or more and 3.3 or less.

<33> The composition according to any one of <1> to <32>, wherein component (a) is one or more selected from the group consisting of a polyvinyl butyral resin and a polyurethane resin.

<34> The composition according to any one of <1> to <33>, wherein component (b) contains ethanol in a content of 80 mass % or more and 100 mass % or less.

<35> The composition according to any one of <1> to <34>, wherein component (c) is one or more selected from the group consisting of an ionic compound and an acyl amino acid ester.

<36> The composition according to any one of <1> to <35>, wherein component (c) is one or more selected from the group consisting of a quaternary ammonium salt, an acyl amino acid salt, an acyl amino acid ester, a homopolymer or copolymer having a (meth)acrylic acid unit, a homopolymer or a copolymer having a primary to tertiary amino group, a homopolymer or a copolymer having a quaternary ammonium group, a homopolymer or a copolymer having an alkyl betaine unit or a sulfobetaine unit, and trimethylglycine.

<37> A method for forming a coating of fibers on a target surface using an electrostatic spraying device holdable by a human hand, comprising a step of electrostatically spraying a composition, for forming a coating of fibers, the composition comprising the following components (a), (b), (c) and (d) onto the target surface:

(a) 1 mass % or more and 45 mass % or less of a polymer having a film-forming ability;

(b) 45 mass % or more and 95 mass % or less of one or more volatile substances selected from the group consisting of an alcohol and a ketone;

(c) a conductivity controlling agent to control the conductivity of the composition to 8 µS/cm or more and 300 µS/cm or less; and (d) 0.2 mass % or more and 25 mass % or less of water.

<38> The method according to <37>, comprising an embodiment according to any one of <2> to <36>.

EXAMPLES

The present invention will be explained in more detail by means of the following examples. However, the scope of the present invention is not limited to these examples. Unless otherwise specified, "%" means "mass %".

Test Example 1

Examples 1 to 16, Comparative Examples 1 to 3

(1) Preparation of Spraying Compositions

As a component (b) of the spraying composition, 99.5% ethanol (manufactured by Wako Pure Chemical Industries, Ltd.) was used. Polyvinyl butyral (manufactured by Sekisui Chemical Co., Ltd.: trade name S-LEC B), polyurethane (Covestro Deutschland AG: trade name Baycusan C2000) was used as component (a). As component (c), the conductivity control agents shown in Tables 1 and 2 were used. Incidentally, the contents of the respective components shown in Tables 1 and 2 are effective amounts, and the units are mass %.

TABLE 1

| | | Example | | | | | | | | | Comparative Example | | |
|---|---|---|---|---|---|---|---|---|---|---|---|---|---|
| | | 1 | 2 | 3 | 4 | 5 | 6 | 7 | 8 | 9 | 1 | 2 | 3 |
| (a) | Polyvinyl butyral (*1) | 11 | 11 | 11 | 11 | 12 | 15 | 11 | 11 | 11 | 11 | 11 | 15 |
| | Distearyldimonium chloride (*2) | 0.01 | 0.1 | 0.5 | 2 | 0.5 | 0.5 | | | | | 3 | |
| (c) | Benzalkonium chloride (*3) | | | | | | | 0.3 | | 0.3 | | | |
| | Palmitoyl sarcosine sodium (*4) | | | | | | | | 0.5 | | | | |
| | Dilauroyl glutamate (phytosteryl/octyldodecyl) (*5) | | | | | 4.8 | | | | | | | |
| (b) | Ethanol | 88.55 | 88.46 | 88.06 | 86.56 | 82.29 | 84.08 | 88.26 | 88.06 | 79.83 | 88.56 | 85.57 | 84.57 |
| (d) | Water | 0.44 | 0.44 | 0.44 | 0.44 | 0.41 | 0.42 | 0.44 | 0.44 | 8.87 | 0.44 | 0.43 | 0.43 |
| | Total | 100.00 | 100.00 | 100.00 | 100.00 | 100.00 | 100.00 | 100.00 | 100.00 | 100.00 | 100.00 | 100.00 | 100.00 |
| | Mass ratio ((c)/(d)) | 0.02 | 0.23 | 1.14 | 4.55 | 1.22 | 1.19 | 0.68 | 1.14 | 0.03 | 0.00 | 6.98 | 0.00 |
| | Viscosity (30° C.) [mPa · s] (X) | 84 | 88 | 88 | 87 | 110 | 256 | 92 | 83 | 99 | 84 | 87 | 268 |
| | Conductivity [µS/cm] (Y) | 10 | 36 | 90 | 257 | 90 | 95 | 109 | 97 | 110 | 5 | 340 | 5 |
| | Y/X | 0.12 | 0.41 | 1.02 | 2.95 | 0.82 | 0.37 | 1.18 | 1.17 | 1.11 | 0.06 | 3.91 | 0.02 |
| | Evaluation | B | A | A | A | A | A | A | A | A | C | C | C |

(*1) S-LEC B BM-1 (Sekisui Chemical Co., Ltd.)
(*2) VARISOFT TA100 (Evonic Japan Co., Ltd.)
(*3) NIKKOL CA101 (50% aqueous solution/effective dose in the table) (Nikko Chemicals Co., Ltd.)
(*4) NIKKOL sarcosinate PN (Nikko Chemicals Co., Ltd.)
(*5) Eldew PS-203 (Ajinomoto Co., Inc.)

TABLE 2

| | | Example 10 | Example 11 | Example 12 | Example 13 | Example 14 | Example 15 | Example 16 |
|---|---|---|---|---|---|---|---|---|
| (a) | Polyvinyl butyral (*1) | 12.0 | 12.0 | 12.0 | | | | |
| | Polyurethane (*8) | | | | 25.0 | 30.0 | 35.0 | 39.8 |
| | Distearyldimonium chloride (*2) | | | | 0.5 | 0.5 | 0.5 | 0.5 |
| | Benzalkonium chloride (*3) | | | | | | | |

TABLE 2-continued

| | | Example 10 | Example 11 | Example 12 | Example 13 | Example 14 | Example 15 | Example 16 |
|---|---|---|---|---|---|---|---|---|
| | N-acyl-L-glutamate triethanolamine (*6) | 0.5 | | | | | | |
| | Cocoyl alanine triethanolamine (*7) | | 0.5 | | | | | |
| | N-methacryloxyl-N,N-dimethyl ammonium-α-N-methylcarboxybetaine/ alkyl methacrylate (*9) | | | 9 | | | | |
| (b) | Ethanol | 87.06 | 87.06 | 78.70 | 74.13 | 69.15 | 64.18 | 59.40 |
| (d) | Water | 0.44 | 0.44 | 0.30 | 0.37 | 0.35 | 0.32 | 0.30 |
| | Total | 100.00 | 100.00 | 100.00 | 100.00 | 100.00 | 100.00 | 100.00 |
| | Mass ratio ((c)/(d)) | 1.14 | 1.14 | 30.00 | 1.35 | 1.43 | 1.56 | 1.67 |
| | Conductivity [μS/cm] | 49 | 47 | 55 | 19 | 38 | 30 | 19 |
| | Evaluation | A | A | B | A | A | A | A |

(*6) Amisoft CT-12S (Ajinomoto Co., Inc.)
(*7) Amilite ACT-12 (Ajinomoto Co., Inc.)
(*8) Baycusan C200040% (the concentrations of in the tables are the efficacious amounts)
(*9) Yucaformer M-75 (Mitsubishi Chemical Co., Ltd.)

Component (a), component (b), component (c), and component (d) were weighed into 1 L glass-made beakers, and stirred at room temperature for about 12 hours using a propeller mixer to obtain uniformly transparent solutions. This was used as a spraying composition.

More specifically, after components (c) and (b) and (d) were mixed, component (a) was added to the mixture, and the resulting mixture was stirred at room temperature using a propeller mixer to obtain a spraying composition.

(2) The Viscosity of the Spraying Composition

After 24 hours of storage at 25° C. after preparation of the spraying composition, it was measured at 25° C. using an E-type viscometer. As the E-type viscometer, an E-type viscometer (VISCONIC EMD) manufactured by Tokyo Meters Co., Ltd. was used, and the rotor No. 43 and the rotational speed of the cone plate were measured at 20 rpm. However, when the viscosity was 150 mPa·s or more, the rotation speed was measured at 10 rpm. The measurement results are given in Table 1.

(3) Conductivity of the Spraying Composition

After the spraying composition was manufactured and stored at 25° C. for 24 hours, the conductivity of the spraying composition of Examples 1 to 16 and Comparative Examples 1 to 3 was measured by an impedance measuring device (SI1260, manufactured by Solartron Distance) under the condition of a measuring terminal (SH-Z), 25° C., φ 10 mm, and distances of 1 mm. The measurement results are shown in Tables 1 and 2.

(2) Electrostatic Spraying Step

The electrostatic spraying step was performed for 30 seconds by using the electrostatic spraying device 10 having the configuration shown in FIG. 1 and the appearance shown in FIG. 2. The conditions of the electrostatic spraying method were as follows. The target object was an aluminum plate (100 mm×100 mm) from the viewpoint of the measurability of the distance and the ease of recognition of the scattering of the spray.

Applied voltage: 10 kV
Distance between nozzle and target object: 80 mm
Volume of spraying composition: 5 mL/h
Environment: 30° C., 70% RH A coating was formed on the surface of the target object by this electrostatic spraying, and evaluated according to the following criteria. The mass of the coating film was about 7 mg.

Evaluation of Sprayability
A: Stable spinning and good fiber coating formation.
a: The fibers are slightly fluffy during spinning. Fibrous membrane formation is possible.
B: Fibers fluctuate during spinning. The formation of fiber membranes is somewhat possible.
C: During spinning, the fibers jump to the periphery. Difficult to form a fiber membrane.

As shown in Tables 1 and 2, as compared with Comparative Examples 1 and 3 in which the conductivity was less than 8 μS/cm and Comparative Example 2 in which the conductivity was more than 300 μS/cm, Examples 1 to 16 were able to form fibrous membranes even in an environment with a humidity of 70% RH, and Examples 2 to 16 were also found to have excellent spinning performance.

The spraying compositions shown in Table 3 were prepared. Specifically, 99.5% ethanol (manufactured by Wako Pure Chemical Industries, Ltd.) was used as component (b) of the spraying composition, polyvinyl butyral (manufactured by Sekisui Chemical Co., Ltd.; trade name S-LEC B) was used as component (a), and the conductivity control agent shown in Table 3 was used as component (c). As shown in Table 3, sufficient conductivity was confirmed in any one of the anionic polymer, the cationic polymer, and the amphoteric polymer. The fiber membranes can also be formed under high humidity for these examples.

TABLE 3

| | | Example 17 | Example 18 | Example 19 |
|---|---|---|---|---|
| (a) | Polyvinyl butyral (*1) | 12.0 | 12.0 | 12.0 |
| | Ethyl acrylate/N-[3-(dimethylamino)propyl]acrylamide/ N-tert-butylacrylamide/methacrylate-α-methylpoly(oxyethylene)-ω-yl- copolymer, poly (N-propanoylethyleneimine)-graft-dimethylsiloxane/γ-aminopropylmethylsiloxane copolymer-monoethyl sulfate (*10) | 10.0 | | |
| | Acrylate/C1-18 alkyl acrylate/C1-8 alkyl acrylamide copolymer AMP (*11) | | | 10.0 |
| | N-methacryloxyl-N,N-dimethylammonium-α-N-methylcarboxy betaine/alkyl methacrylate (*9) | | 12 | |

TABLE 3-continued

|  |  | Example 17 | Example 18 | Example 19 |
|---|---|---|---|---|
| (b) | Ethanol | 77.60 | 75.76 | 77.60 |
| (d) | Water | 0.40 | 0.24. | 0.40 |
|  | Total | 100.00 | 100.00 | 100.00 |
|  | Mass ratio (c/d) | 25.00 | 50.00 | 25.00 |
|  | Conductivity [µs/cm] | 13 | 61 | 24 |

(*10) oxazoline-modified silicone polymer manufactured by the method described in JP-A-1990-276824.
(*11) Plassize L-9909B (GK909) manufactured by Goo Chemical Co., Ltd.

EXPLANATION OF SYMBOLS

10 Electrostatic spraying device
11 Low-voltage power supply
12 High-voltage power supply
13 Auxiliary electrical circuit
14 Microgear pump
15 Container
16 Nozzle
17 Pipe
18 Flexible pipe
19 Current limit resistor
20 Housing

The invention claimed is:

1. A method for forming a coating of continuous fibers on a target object by electrostatic spraying using an electrostatic spraying device holdable by a human hand, the method comprising electrostatically spraying a composition comprising the following components (a), (b), (c) and (d):
   (a) 1 mass % or more and 30 mass % or less of one or more water-insoluble polymer polymers having a film-forming ability wherein at least one of said one or more water-insoluble polymers is a polyvinyl butyral resin, the polymer being soluble in component (b);
   (b) 50 mass % to 94 mass % of one or more volatile substances selected from the group consisting of an alcohol and a ketone;
   (c) a conductivity controlling agent to control the conductivity of the composition to 10 µS/cm or more and 300 µS/cm or less, the conductivity controlling agent being selected from the group consisting of a cationic surfactant and an anionic surfactant; and
   (d) 0.2 mass % or more and 25 mass % or less of water, wherein the fibers are formed by volatilizing the component (b) before the sprayed composition reaches the target object or immediately after the sprayed composition is attached to the object.

2. The method according to claim 1, wherein the composition has a viscosity of from 2 to 3,000 mPa·s at 25° C.

3. The method according to claim 1, wherein the content of component (c) is 0.01 mass % or more and 10 mass % or less.

4. The method according to claim 1, wherein the target object is skin.

5. The method according to claim 1, wherein the content of component (a) in the composition is 2 mass % or more and 25 mass % or less, and
   the content of component (b) in the composition is 50 mass % or more and 92 mass % or less.

6. The method according to claim 1, wherein in component (a) said one or more water-insoluble polymers is a mixture of (i) a polyvinyl butyral resin and (ii) an additional water-insoluble polymer selected from the group consisting of a fully-saponified or partially-saponified polyvinyl alcohol, a polyurethane resin, an oxazoline-modified silicone, a polyester, and Zein.

7. The method according to claim 1, wherein in component (a) said one or more water-insoluble polymers is a mixture of a polyvinyl butyral resin and a polyurethane resin.

8. The method according to claim 1, wherein the mass ratio of component (c) to component (d), ((c)/(d)), is 0.01 or more and 6 or less.

9. The method according to claim 1, wherein a content of powder is 1 mass % or less.

10. The method according to claim 1, wherein the fiber has a length of at least 100 times or more of the thickness of the fiber.

11. The method according to claim 1, wherein the conductivity of the composition is 10 µS/cm or more and 260 µS/cm or less.

12. The method according to claim 1, wherein the thickness of the fiber is 10 nm or more and 3,000 nm or less when expressed as a circle equivalent diameter.

* * * * *